US011646188B2

(12) United States Patent  
Hirose et al.

(10) Patent No.: US 11,646,188 B2  
(45) Date of Patent: May 9, 2023

(54) APPARATUS AND METHOD FOR ANALYZING EVOLVED GAS

(71) Applicant: HITACHI HIGH-TECH SCIENCE CORPORATION, Tokyo (JP)

(72) Inventors: Ryusuke Hirose, Tokyo (JP); Hideyuki Akiyama, Tokyo (JP); Noriaki Sakai, Tokyo (JP); Masafumi Watanabe, Tokyo (JP)

(73) Assignee: HITACHI HIGH-TECH SCIENCE CORPORATION, Tokyo (JP)

( * ) Notice: Subject to any disclaimer, the term of this patent is extended or adjusted under 35 U.S.C. 154(b) by 60 days.

(21) Appl. No.: 16/041,683

(22) Filed: Jul. 20, 2018

(65) Prior Publication Data

US 2019/0027353 A1    Jan. 24, 2019

(30) Foreign Application Priority Data

Jul. 21, 2017   (JP) .............................. JP2017-142233

(51) Int. Cl.
| | |
|---|---|
| *H01J 49/04* | (2006.01) |
| *H01J 49/00* | (2006.01) |
| *G01N 33/00* | (2006.01) |
| *G01N 33/44* | (2006.01) |

(52) U.S. Cl.  
CPC ...... *H01J 49/0422* (2013.01); *G01N 33/0021* (2013.01); *H01J 49/0031* (2013.01); *G01N 33/442* (2013.01)

(58) Field of Classification Search  
CPC .............. H01J 49/0031; H01J 49/0422; G01N 33/0021; G01N 33/442  
See application file for complete search history.

(56) References Cited

U.S. PATENT DOCUMENTS

| 4,361,810 A | * | 11/1982 | Schlosser ........... G01N 33/0022 |
| | | | 324/468 |
| 5,624,846 A | * | 4/1997 | Hayashibe ........... G01N 35/085 |
| | | | 422/108 |
| 5,986,259 A | * | 11/1999 | Hirabayashi .......... H01J 49/044 |
| | | | 250/281 |

(Continued)

FOREIGN PATENT DOCUMENTS

| JP | 09-311128 A | 12/1997 |
| JP | 09311128 A | * 12/1997 |

(Continued)

*Primary Examiner* — David E Smith  
(74) *Attorney, Agent, or Firm* — Holland & Hart LLP (57) ABSTRACT

Disclosed is an apparatus and method for analyzing an evolved gas, wherein the precision of detection of a gas component is improved without enlarging the apparatus. The apparatus includes a gas component evolving unit, a detection member for detecting the gas component, and a mixed gas channel for allowing a mixed gas containing the gas component and carrier gas to flow therethrough, and further includes a branch channel branched from the mixed gas channel, an inert gas channel for allowing an inert gas to flow therethrough, a first flow rate regulator for adjusting the flow rate of the carrier gas, a second flow rate regulator for adjusting the flow rate of the inert gas, and a flow rate control unit for controlling the second flow rate regulator such that the flow rate of the mixed gas guided to the detection member is a predetermined value.

6 Claims, 7 Drawing Sheets

(56) References Cited

U.S. PATENT DOCUMENTS

| | | | | |
|---|---|---|---|---|
| 2013/0062515 A1* | 3/2013 | Quimby | ............. | H01J 49/0422 |
| | | | | 250/288 |
| 2016/0061798 A1* | 3/2016 | Wapelhorst | ......... | H01J 49/0422 |
| | | | | 73/23.2 |
| 2016/0233067 A1* | 8/2016 | Gordon | ............... | H01J 49/0422 |
| 2016/0298783 A1* | 10/2016 | Chun | .................... | F16K 31/025 |
| 2016/0320294 A1* | 11/2016 | Schlueter | .................. | G01F 1/00 |

FOREIGN PATENT DOCUMENTS

| | | | |
|---|---|---|---|
| JP | 10239280 | A | 9/1998 |
| JP | 2001-028251 | A | 1/2001 |
| JP | 2012-202887 | A | 10/2012 |
| JP | 2017021031 | A | 1/2017 |
| JP | 2017102102 | A | 6/2017 |

\* cited by examiner

APPARATUS AND METHOD FOR ANALYZING EVOLVED GAS

CROSS REFERENCE TO RELATED APPLICATION

This application claims priority to and the benefit of Japanese Patent Application No. JP 2017-142233, by HIROSE et al., filed Jul. 21, 2017, which is hereby incorporated by reference in its entirety into this application.

BACKGROUND OF THE INVENTION

1. Technical Field

The present invention relates to an apparatus and method for analyzing an evolved gas, in which a gas component evolved by heating a sample may be analyzed, thus identifying or quantifying the sample.

2. Description of the Related Art

In order to ensure the flexibility of a resin, the resin may contain, as a plasticizer, phthalate esters (commonly known as phthalates), but the use of four kinds of phthalates will be restricted starting in 2019 under the Restriction of Hazardous Substances (RoHS) adopted by the European Union. Hence, phthalates in resin are required to be identified and quantified.

Phthalates, which are volatile, may be analyzed through conventionally known EGA (Evolved Gas Analysis). EGA is used to analyze a gas component, evolved by heating a sample, using any type of analysis apparatus, such as a gas chromatograph or a mass spectrometer.

For evolved gas analysis, an evolved gas component is made to flow in a carrier gas such as nitrogen gas or the like and is introduced in that state into an analysis apparatus. However, when the gas component is evolved in a large amount and thus the gas concentration becomes too high, a detection signal of the analysis apparatus exceeds the detection range thereof and thus is over-scaled, making it difficult to realize accurate measurement.

Accordingly, there has been disclosed a technique for reducing the gas concentration by diluting the gas component in a manner in which the flow rate of the carrier gas that is to be mixed with the gas component is increased when the detection signal of the analysis apparatus exceeds the detection range (Patent Documents 1 and 2). Also disclosed is a technique for selectively detecting a gas component, which is an analysis target, in which a purge gas is introduced into a measurement system, whereby gases other than the analysis target are purged and thus discharged out of the system (Patent Document 3).

CITATION LIST

Patent Literature (Patent Document 1) Japanese Patent Application Publication No. 2001-28251
(Patent Document 2) Japanese Patent Application Publication No. 2012-202887
(Patent Document 3) Japanese Patent Application Publication No. 1997-311128

SUMMARY OF THE INVENTION

However, the technique disclosed in Patent Documents 1 and 2 is problematic because the flow rate of the carrier gas is increased when the gas concentration is high, and thus the supply capacity of the carrier gas has to be increased, undesirably raising the size of the analysis apparatus and the cost therefor.

Also, when a mass spectrometer is used as the analysis apparatus, the gas component is ionized at the front thereof. However, when the gas component contains an accessory component that is not the measurement target, the accessory component is also ionized. In the case where the gas component is evolved in a large amount, the original component of the measurement target to be ionized is not sufficiently ionized and the detection signal of the measurement target is somewhat degraded (ion suppression). In this case, it is difficult to use the technique disclosed in Patent Documents 1 and 2.

Moreover, in the technique disclosed in Patent Document 3, the purge gas introduced into the measurement system flows in a direction reverse to the direction of flow of the gas component and carrier gas due to the fluid resistance of a capillary separation column, serving as a detector, and is then discharged from the upstream split vent (branch pipe). However, in the process using such reverse flow, emission of gas components other than the analysis target becomes possible, but it is impossible to adjust the concentration of the gas component with the carrier gas, and it is also difficult to accurately adjust the flow rate of gas introduced into the detector, thus making it difficult to improve the precision of detection.

Accordingly, the present invention has been made keeping in mind the problems encountered in the related art, and the present invention is intended to provide an apparatus and method for analyzing an evolved gas, in which the precision of detection of a gas component may be improved without the need to enlarge the apparatus.

Therefore, the present invention provides an apparatus for analyzing an evolved gas, comprising: a gas component evolving unit configured to evolve a gas component contained in a sample, a detection member configured to detect the gas component evolved from the gas component evolving unit, and a mixed gas channel configured to connect the gas component evolving unit and the detection member to each other and to allow a mixed gas comprising the gas component and a carrier gas for guiding the gas component to the detection member to flow therethrough, and further comprising: a branch channel branched from the mixed gas channel and open to the outside, an inert gas channel joined to the mixed gas channel at a junction downstream of the branch channel such that an inert gas is allowed to flow therethrough, a first flow rate regulator configured to adjust a flow rate $F1$ of the carrier gas, a second flow rate regulator configured to adjust a flow rate $F4$ of the inert gas flowing through the inert gas channel, and a flow rate control unit configured to control the second flow rate regulator such that a flow rate of the mixed gas guided to the detection member is a predetermined value.

In the apparatus for analyzing an evolved gas according to the present invention, the inert gas is allowed to flow in the mixed gas channel downstream of the branch channel, whereby flow resistance that suppresses the flow rate of the mixed gas introduced into the detection member may result, thus adjusting the flow rate of the mixed gas discharged from the branch channel. Specifically, when the flow rate $F4$ of the inert gas is adjusted using the second flow rate regulator, the ratio (split ratio) of the mixed gas discharged from the branch channel may be controlled. For example, compared to when the split ratio is controlled by adjusting the diameter (flow resistance) of the mixed gas channel and the branch channel, good efficiency may be obtained, no limitations are imposed on setting the flow resistance due to the dimensions of the apparatus, and the split ratio may be easily adjusted.

Furthermore, when the split ratio is physically controlled by the diameter (flow resistance) of the mixed gas channel and the branch channel, it is difficult to change the split ratio in subsequent procedures, but in the present invention, the split ratio may be freely controlled in subsequent procedures by adjusting the flow rate using the second flow rate regulator.

When the gas component is generated in a large amount and thus the gas concentration becomes too high, the flow rate of the mixed gas discharged from the branch channel to the outside is increased, whereby the flow rate of the mixed gas introduced from the gas channel to the detection member is reduced. Accordingly, the problem of inaccurate measurement due to over-scale of the detection signal that exceeds the detection range of the detection member may be solved.

Here, the inert gas is allowed to flow only in a relatively small amount due to the flow resistance, and there is no need to increase the flow rate of the carrier gas or the flow rate of the inert gas, and thus the precision of detection of the gas component may be improved without increasing the supply capacity of carrier gas or inert gas and without enlarging the apparatus. Moreover, there is no need to dilute the gas concentration with a large amount of carrier gas or inert gas, and an enlargement in the apparatus to accommodate an increased amount of gas introduced into the detection member may be prevented.

In the apparatus for analyzing an evolved gas according to the present invention, a discharge pressure regulator for adjusting the discharge pressure of the mixed gas discharged from the branch channel may be provided at the discharge side of the branch channel.

Also, in the pipe in which the discharge side of the branch channel is exposed, the flow rate of the mixed gas discharged from the branch channel may vary due to variation in atmospheric pressure with climate. Thus, in the apparatus for analyzing an evolved gas according to the present invention, the discharge pressure of the mixed gas discharged from the branch channel is adjusted using the discharge pressure regulator (the mixed gas is discharged from the branch channel when exceeding a predetermined pressure), whereby the influence of variation in atmospheric pressure may be suppressed, thus further improving the precision of detection of the gas component.

In the apparatus for analyzing an evolved gas according to the present invention, the detection member is a mass spectrometer, and an ion source is provided between the mixed gas channel and the mass spectrometer so as to ionize the gas component of the mixed gas.

The flow rate control unit may control the first flow rate regulator so as to increase the flow rate F1 when a detection signal from the detection member is less than a predetermined range.

When a mass spectrometer is used as an analysis apparatus in the present invention, the gas component is ionized by the ion source at the front thereof. However, when the gas component is generated in a large amount, a large amount of accessory component is also ionized, and thus ion suppression, in which the original component to be measured is not sufficiently ionized and the detection signal of the measurement target is somewhat degraded, occurs, and the detection signal is also degraded.

Hence, in the apparatus for analyzing an evolved gas according to the present invention, when ion suppression occurs, the flow rate control unit determines the peak intensity of the detection signal to be less than the threshold value, thereby controlling the first flow rate regulator so that the discharge flow rate of the mixed gas is increased. Accordingly, the flow rate of the mixed gas introduced into the ion source is decreased, and thus the ionization of the accessory component is suppressed, and the degradation of the detection signal is also prevented, thereby improving the precision of detection of the gas component.

The apparatus for analyzing an evolved gas according to the present invention may further comprise a flow rate measurement instrument for measuring the flow rate of the mixed gas flowing into the junction or the flow rate of the mixed gas discharged from the branch channel.

When the mass spectrometer is used as the analysis apparatus, a flow meter cannot be provided between the ion source and the mass spectrometer, making it difficult to directly measure the flow rate of the mixed gas introduced into the mass spectrometer. Therefore, the flow rate of the mixed gas flowing into the junction or the flow rate of the mixed gas discharged from the branch channel is measured, whereby the flow rate of the mixed gas introduced into the mass spectrometer may be indirectly calculated and thus may be determined in real time.

In addition, the present invention provides a method of analyzing an evolved gas using an apparatus for analyzing an evolved gas comprising a gas component evolving unit configured to evolve a gas component contained in a sample, a detection member configured to detect the gas component evolved from the gas component evolving unit, and a mixed gas channel configured to connect the gas component evolving unit and the detection member to each other and to allow a mixed gas comprising the gas component and a carrier gas for guiding the gas component to the detection member to flow therethrough, the apparatus further comprising a branch channel branched from the mixed gas channel and open to the outside and an inert gas channel joined to the mixed gas channel at a junction downstream of the branch channel such that an inert gas is allowed to flow therethrough, the method comprising: primarily adjusting a flow rate F1 of the carrier gas, secondarily adjusting a flow rate F4 of the inert gas flowing through the inert gas channel, and controlling the secondarily adjusting so that the flow rate of the mixed gas guided to the detection member is a predetermined value.

According to the present invention, the precision of detection of a gas component can be improved without the need to increase the size of an apparatus for analyzing an evolved gas.

DESCRIPTION OF SPECIFIC EMBODIMENTS

Figure 1:
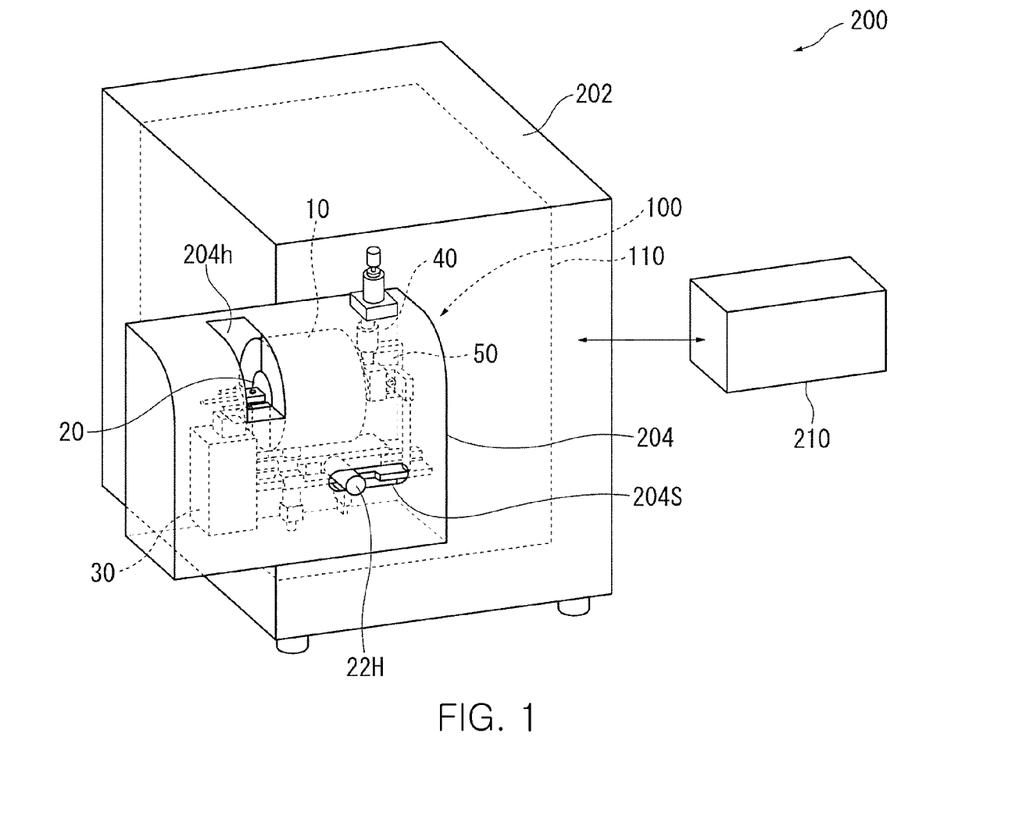
FIG. 1 is a perspective view showing the configuration of an apparatus for analyzing an evolved gas according to an embodiment of the present invention.
Figure 2:
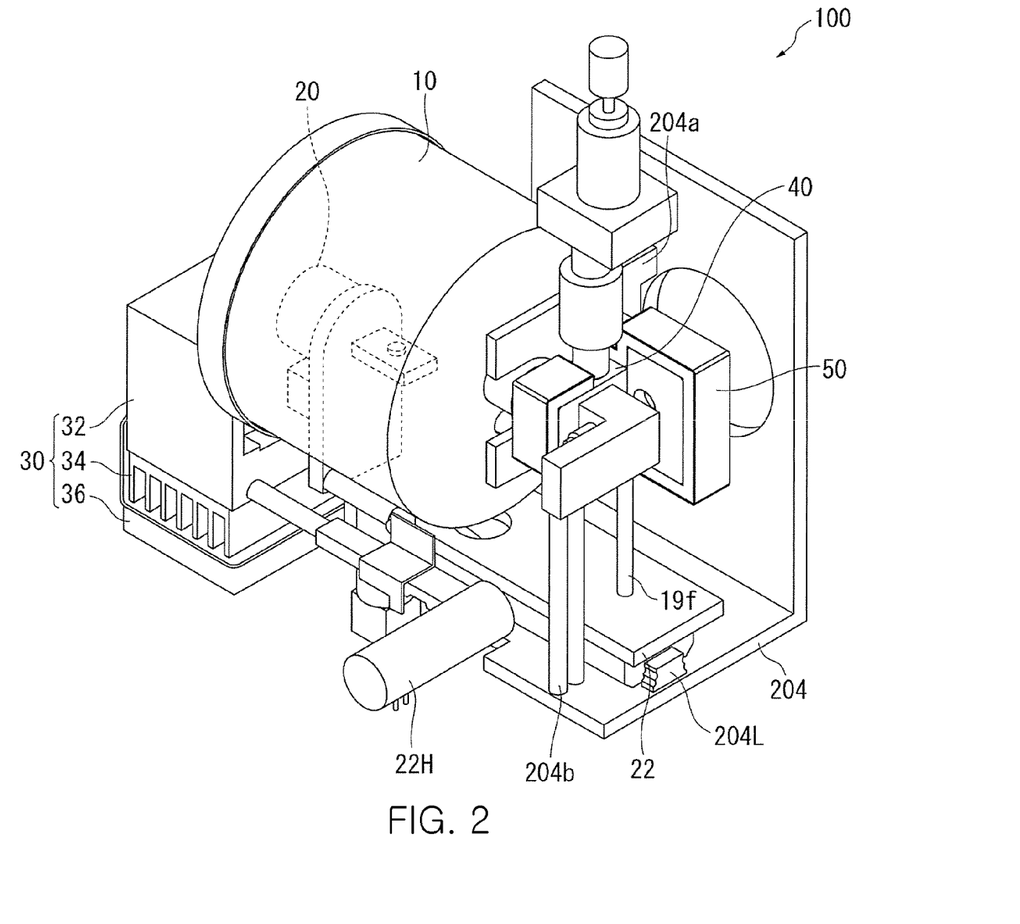
FIG. 2 is a perspective view showing the configuration of a gas evolving unit.
Figure 3:
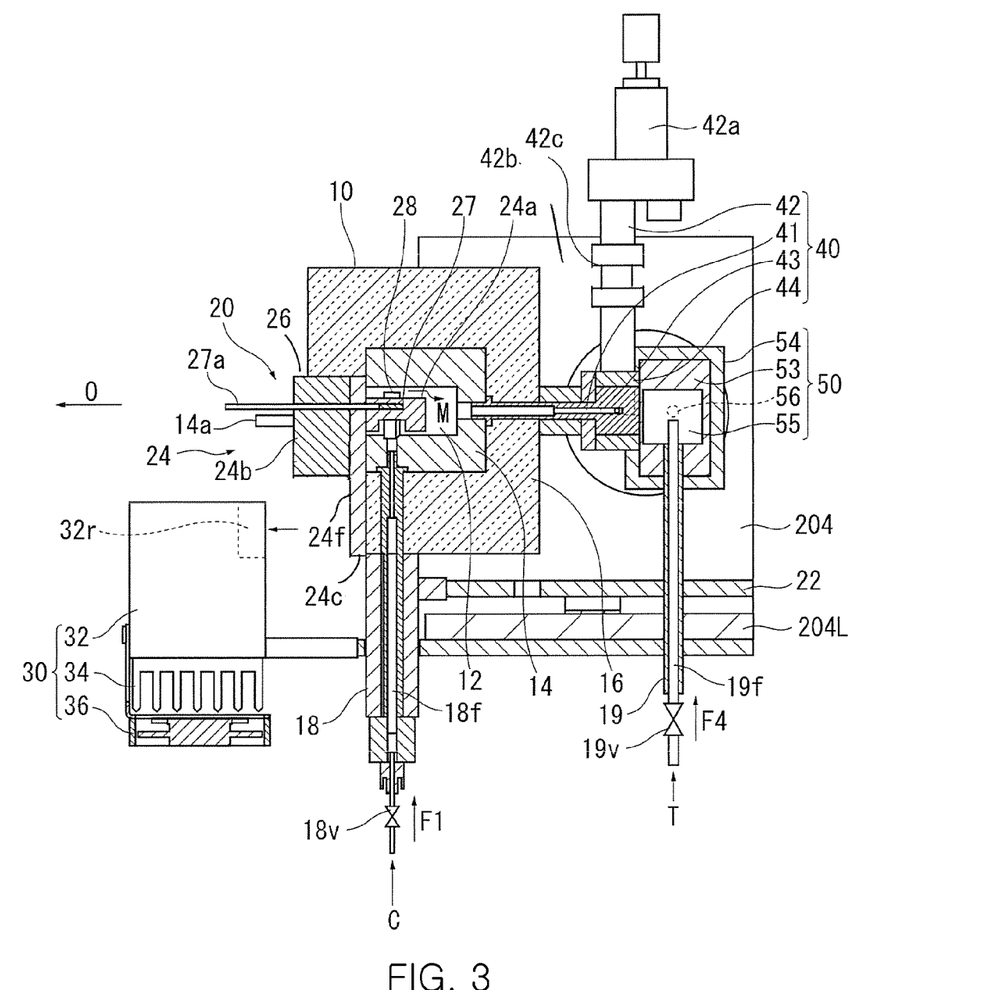
FIG. 3 is a longitudinal cross-sectional view showing the configuration of the gas evolving unit.
Figure 4:
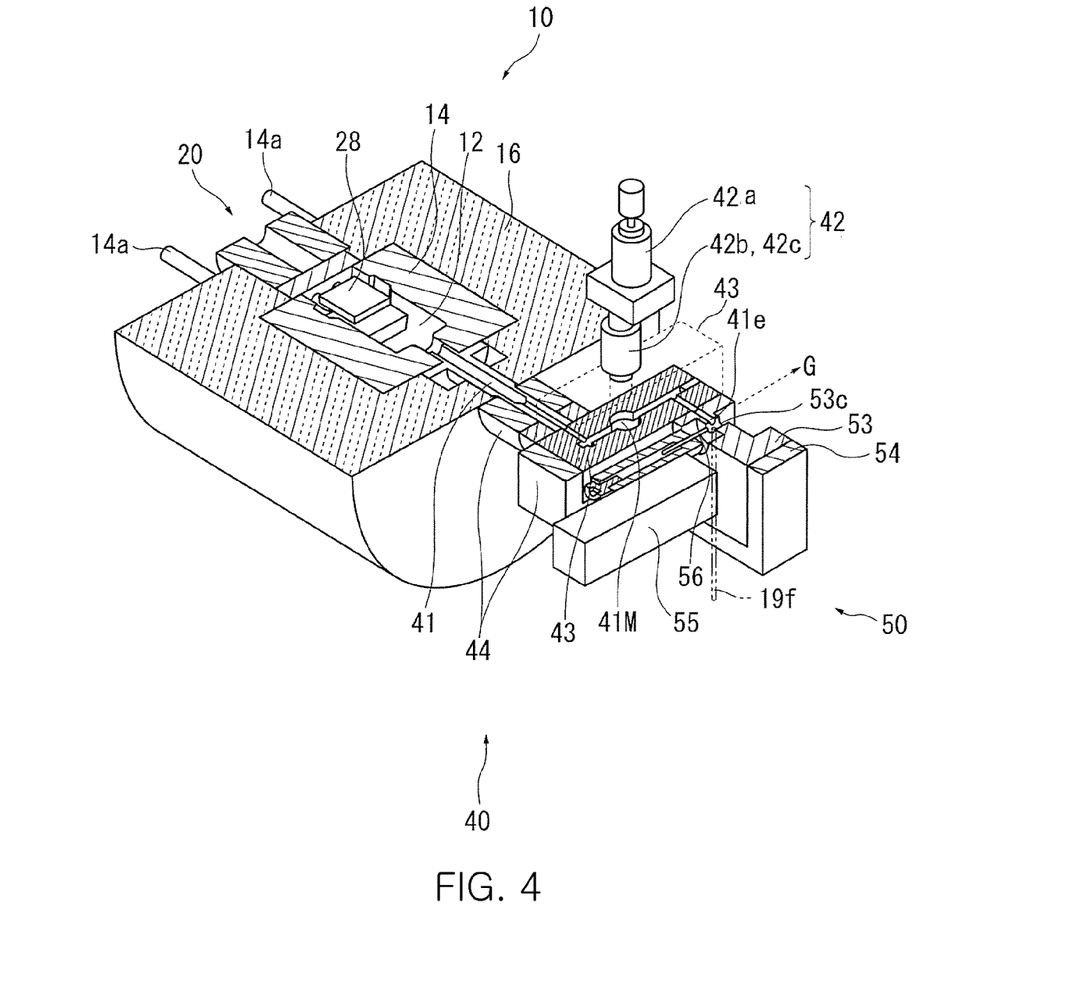
FIG. 4 is a transverse cross-sectional view showing the configuration of the gas evolving unit.
Figure 5:
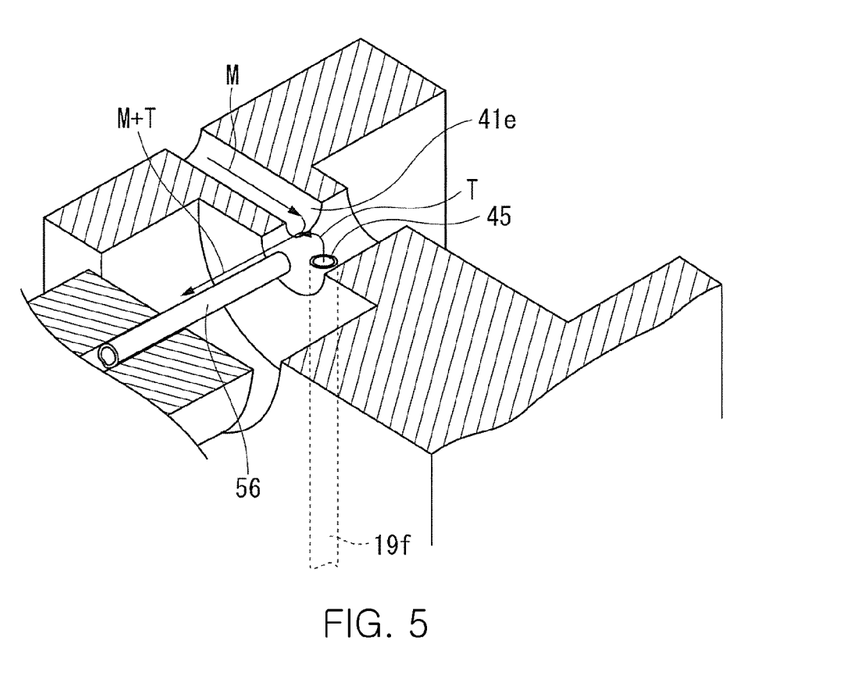
FIG. 5 is a partially enlarged view of FIG. 4.

Hereinafter, a detailed description will be given of embodiments of the present invention with reference to the appended drawings. FIG. 1 is a perspective view showing the configuration of an apparatus 200 for analyzing an evolved gas according to an embodiment of the present invention, FIG. 2 is a perspective view showing the configuration of a gas evolving unit 100, FIG. 3 is a longitudinal cross-sectional view showing the configuration of the gas evolving unit 100 on an axis O, FIG. 4 is a transverse cross-sectional view showing the configuration of the gas evolving unit 100 on the axis O, and FIG. 5 is a partially enlarged view of FIG. 4.

The apparatus 200 for analyzing an evolved gas includes a body unit 202, which is a housing, a box-shaped gas-evolving-unit attachment unit 204 attached to the front of the body unit 202, and a computer (control unit) 210 for controlling the entire apparatus. The computer 210 includes a CPU for data processing, a memory unit for storing a computer program or data, a monitor, and input units such as a keyboard, etc.

The gas-evolving-unit attachment unit 204 accommodates therein a gas evolving unit 100 configured such that a cylindrical heating furnace 10, a sample holder 20, a cooler 30, a splitter 40 for gas splitting, an ion source 50, and an inert gas channel 19f are assembled together. Also, the body unit 202 accommodates therein a mass spectrometer 110 for analyzing a gas component evolved by heating a sample.

The heating furnace 10 is referred to as a ⌈ gas component evolving unit ⌋ in the claims, and the mass spectrometer 110 is referred to as a ⌈ detection member ⌋ in the claims.

As shown in FIG. 1, an opening 204h is formed in the forward direction from the upper surface of the gas-evolving-unit attachment unit 204, and when the sample holder 20 is moved to the discharge position (which will be described later) outside the heating furnace 10, it is located at the opening 204h, whereby the sample may be placed in or taken out of the sample holder 20 via the opening 204h. Furthermore, a slit 204s is formed in the front of the gas-evolving-unit attachment unit 204, and the sample holder 20 is moved into or out of the heating furnace 10 by moving an opening/closing handle 22H exposed to the outside through the slit 204s in opposite directions, and is thus set to the above discharge position, whereby the sample may be placed in or taken out of the sample holder.

Also, for example, when the sample holder 20 is moved on a movement rail 204L (which will be described later) by means of a stepping motor, etc. controlled by the computer 210, the sample holder 20 may be automatically moved into or out of the heating furnace 10.

With reference to FIGS. 2 to 6, the configuration of the gas evolving unit 100 is described in detail below.

The heating furnace 10 is attached to the attachment plate 204a of the gas-evolving-unit attachment unit 204 in the state in which it is parallel to the axis O, and includes a heating chamber 12 having a substantially cylindrical shape, which is open on the axis O, a heating block 14, and a heat retaining jacket 16.

The heating block 14 is disposed on the outer surface of the heating chamber 12, and the heat retaining jacket 16 is disposed on the outer surface of the heating block 14. The heating block 14 is made of aluminum, and is heated through electrical conduction using a pair of heater electrodes 14a (FIG. 4) extending to the outside of the heating furnace 10 along the axis O.

Also, the attachment plate 204a extends in a direction perpendicular to the axis O, and the splitter 40 and the ion source 50 are attached to the heating furnace 10. Furthermore, the ion source 50 is supported by a support 204b extending in the vertical direction of the gas-evolving-unit attachment unit 204.

The splitter 40 is connected to a position (at the right of FIG. 3) opposite the opening of the heating furnace 10. Also, a carrier gas protection pipe 18 is connected to the bottom of the heating furnace 10, and the carrier gas protection pipe 18 accommodates therein a carrier gas channel 18f that communicates with the lower surface of the heating chamber 12 to thus supply a carrier gas C to the heating chamber 12. The carrier gas channel 18f is provided with a control valve 18v for controlling the flow rate F1 of the carrier gas C.

Although the details thereof will be described later, a mixed gas channel 41 communicates with the end surface of the heating chamber 12 (at the right of FIG. 3) opposite the opening thereof, whereby a mixed gas M comprising the gas component G generated from the heating furnace 10 (heating chamber 12) and the carrier gas C is allowed to flow through the mixed gas channel 41.

Meanwhile, as shown in FIG. 3, an inert gas protection pipe 19 is connected to the bottom of the ion source 50, and the inert gas protection pipe 19 accommodates therein an inert gas channel 19f for supplying an inert gas T to the ion source 50. Furthermore, the inert gas channel 19f is provided with a control valve 19v for controlling the flow rate F4 of the inert gas T.

The control valves 19v are referred to as a ⌈ first flow rate regulator ⌋ and a ⌈ second flow rate regulator ⌋, respectively, in the claims.

The inert gas may include, for example, nitrogen or rare gas such as argon, and is a gas that is not reactive, flammable and corrosive.

The sample holder 20 includes a stage 22 moving on the movement rail 204L attached to the inner upper surface of the gas-evolving-unit attachment unit 204, a bracket 24c attached onto the stage 22 and extending vertically, heat insulators 24b, 26 attached to the front of the bracket 24c (at the left of FIG. 3), a sample-holding unit 24a extending from the bracket 24c to the heating chamber 12 in the direction of the axis O, a heater 27 provided directly under the sample-holding unit 24a, and a sample plate 28 disposed at the upper surface of the sample-holding unit 24a directly above the heater 27 so as to receive the sample.

Here, the movement rail 204L extends in the direction of the axis O (the horizontal direction in FIG. 3), and the stage 22 of the sample holder 20 moves in the direction of the axis O. Furthermore, the opening/closing handle 22H is attached to the stage 22 while extending in a direction perpendicular to the axis O.

Also, the bracket 24c has a long rectangular shape having a semicircular upper portion, and the heat insulator 24b has a substantially cylindrical shape and is attached to the front surface of the upper portion of the bracket 24c (FIG. 3), and the electrode 27a of the heater 27 protrudes outwards through the heat insulator 24b. The heat insulator 26 has a substantially rectangular shape, and is provided to the front surface of the bracket 24c at a position lower than the heat insulator 24b. The lower portion of the bracket 24c is not provided with the heat insulator 26, and the front surface of the bracket 24c is exposed to form a contact surface 24f.

The bracket 24c has a diameter slightly greater than that of the heating chamber 12 such that the heating chamber 12 is hermetically sealed, and the sample-holding unit 24a is accommodated in the heating chamber 12.

The sample placed on the sample plate 28 in the heating chamber 12 is heated in the heating furnace 10, thus generating the gas component G.

The cooler 30 is disposed to face the bracket 24c of the sample holder 20 and is located outside the heating furnace 10 (to the left of the heating furnace 10 in FIG. 3). The cooler 30 includes a cooling block 32 having a recess 32r with a substantially rectangular shape, a cooling fin 34 connected to the lower surface of the cooling block 32, and an air-cooling fan 36 connected to the lower surface of the cooling fin 34 so as to blow air to the cooling fin 34.

When the sample holder 20 moves toward the left of FIG. 3 in the direction of the axis O along the movement rail 204L and exits the heating furnace 10, the contact surface 24f of the bracket 24c comes into contact with the recess 32r in the cooling block 32 while being accommodated in the recess 32r, whereby heat is dissipated from the bracket 24c through the cooling block 32 to thus cool the sample holder 20 (in particular, the sample-holding unit 24a).

In an embodiment of the present invention, the sample holder 20 (including the bracket 24c) and the cooling block 32 are made of aluminum.

As shown in FIGS. 3 and 4, the splitter 40 includes the mixed gas channel 41 communicating with the heating chamber 12, a branch channel 42 branched by a predetermined branch portion (a channel block branch) from the mixed gas channel 41 and open to the outside while communicating with the mixed gas channel 41, a flow meter 42c connected to the discharge side of the branch channel 42 and configured to measure the flow rate of the mixed gas M discharged from the branch channel 42, a back pressure valve 42a for adjusting the discharge pressure, a housing unit 43 in which the longitudinal end of the mixed gas channel 41 is open, and a heat retaining unit 44 surrounding the housing unit 43.

In the present embodiment, a filter 42b is interposed between the branch channel 42 and the flow meter 42c so as to remove impurities from the mixed gas.

The back pressure valve 42a functions to adjust the discharge pressure at which the mixed gas is discharged from the branch channel 42. Here, the back pressure valve 42a and the flow meter 42c are referred to as a ⌈discharge pressure regulator⌋ and a ⌈flow rate measurement instrument⌋, respectively, in the claims. As the back pressure valve 42a, any commercially available example thereof may be used.

Also, in the present embodiment, the discharge side of the branch channel 42 is not provided with a member (e.g. a vacuum pump, etc.) by which negative pressure is actively generated to promote discharge. Accordingly, the need for a vacuum pump, etc. is obviated, thus reducing costs. Also, a pipe, which is not provided with a valve for adjusting discharge pressure, such as the back pressure valve 42a, and to which the end of the branch channel 42 is exposed, may be an example thereof.

As shown in FIG. 4, when viewed from above, the mixed gas channel 41 is provided in the shape of a crank in a manner that extends in the direction of the axis O while communicating with the heating chamber 12, is bent perpendicular to the direction of the axis O, and is also bent in the direction of the axis O to reach a longitudinal end part 41e. Furthermore, the center of the portion of the mixed gas channel 41 extending perpendicular to the direction of the axis O is enlarged in the diameter thereof to form a branch chamber 41M. The branch chamber 41M extends to the top of the housing unit 43, and the branch channel 42, having a diameter slightly smaller than that of the branch chamber 41M, is fitted thereto.

The mixed gas channel 41 may be provided in the form of a straight line that reaches the longitudinal end part 41e by extending in the direction of the axis O while communicating with the heating chamber 12, or may be provided in the form of any curved shape or a linear shape having an angle with respect to the axis O depending on the position of the heating chamber 12 or the ion source 50.

As shown in FIGS. 3 and 4, the ion source 50 includes a housing unit 53, a heat retaining unit 54 surrounding the housing unit 53, an electric discharge needle 56, and a staying unit 55 for fixing the electric discharge needle 56. The housing unit 53 has a plate shape, and the surface of the plate is parallel to the axis O, and a small hole 53c is formed in the center of the surface of the plate. The longitudinal end part 41e of the mixed gas channel 41 faces the side wall of the small hole 53c through the inside of the housing unit 53. The electric discharge needle 56 extends in a direction perpendicular to the axis O and thus faces the small hole 53c.

As shown in FIGS. 4 and 5, the inert gas channel 19f vertically penetrates the housing unit 53, and the tip of the inert gas channel 19f faces the bottom of the small hole 53c in the housing unit 53 and forms a junction 45 that joins the longitudinal end part 41e of the mixed gas channel 41.

The mixed gas M introduced to the junction 45 near the small hole 53c from the longitudinal end part 41e is mixed with the inert gas T from the inert gas channel 19f to thus form a combined gas M+T, which is then made to flow toward the electric discharge needle 56. Of the combined gas M+T, the gas component G is ionized by the electric discharge needle 56.

The ion source 50 is a known device, and in the present embodiment, an atmospheric pressure chemical ionization (APCI)-type ion source is adopted. APCI does not readily fragment the gas component G and does not generate fragment peaks, and is desirably used because a measurement target may be detected even without separation through chromatography.

The gas component G ionized by the ion source 50 is introduced together with the carrier gas C and the inert gas T into the mass spectrometer 110 and is thus analyzed.

The ion source 50 is accommodated in the heat retaining unit 54.

Figure 6:
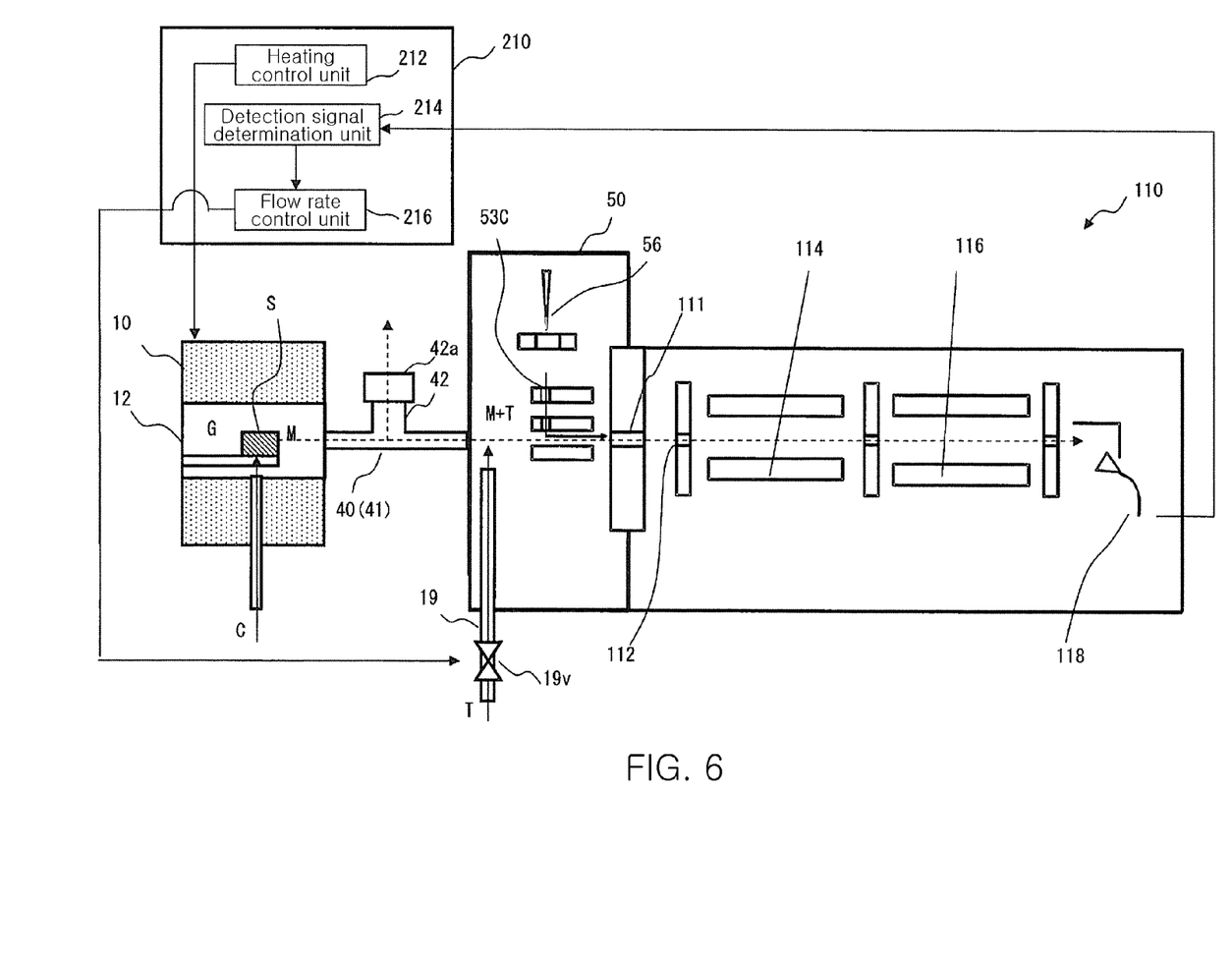
FIG. 6 is a block diagram showing a process of analyzing a gas component using the apparatus for analyzing an evolved gas.

FIG. 6 is a block diagram showing the process of analyzing the gas component using the apparatus 200 for analyzing an evolved gas.

A sample S is heated in the heating chamber 12 of a heating furnace 10, thus generating a gas component G. The heating state (heating rate, maximum temperature, etc.) of the heating furnace 10 is controlled by the heating control unit 212 of the computer 210.

The gas component G is mixed with the carrier gas C introduced into the heating chamber 12 to form a mixed gas M, which is then supplied to the splitter 40, and a portion of the mixed gas M is emitted outside from the branch channel 42.

To the ion source 50, the remainder of the mixed gas M and the inert gas T from the inert gas channel 19f are supplied as the combined gas M+T, and the gas component G is ionized therein.

The detection signal determination unit 214 of the computer 210 receives a detection signal from the detector 118 (which will be described later) of the mass spectrometer 110.

The flow rate control unit 216 determines whether the peak intensity of the detection signal received in the detection signal determination unit 214 falls outside of a threshold range. When the peak intensity is determined to fall outside of the threshold range, the flow rate control unit 216 controls the opening ratio of the control valve 19v, whereby the flow rate of the mixed gas M discharged outside from the branch channel 42 in the splitter 40, particularly the flow rate of the mixed gas M introduced to the ion source 50 from the mixed gas channel 41, is adjusted, thus maintaining the maximum precision of detection of the mass spectrometer 110.

The mass spectrometer 110 includes a first aperture 111, through which the gas component G ionized in the ion source 50 is introduced, a second aperture 112, through which the gas component G flows after flowing through the first aperture 111, an ion guide 114, a quadrupole mass filter 116, and a detector 118 for detecting the gas component G discharged from the quadrupole mass filter 116.

The quadrupole mass filter 116 varies an applied high frequency voltage to thus enable mass scanning, and generates a quadrupole electric field and thus detects ions by subjecting the ions to vibratory motion within the quadrupole electric field. The quadrupole mass filter 116 functions as a mass separator that transmits only the gas component G within a certain mass range such that the detector 118 may identify and quantify the gas component.

Also, in comparison with an entire ion detection (scan) mode for detecting ions of a mass-to-charge ratio in any range, when using a selected ion monitoring (SIM) mode for detecting only ions of a certain mass-to-charge ratio (m/z) of a gas component, which is a measurement target, the precision of detection of the gas component, which is the measurement target, may increase.

Also, the mass spectrometer 110 becomes negative pressure (vacuum suction), and the flow rate F5 (FIG. 7) of the mixed gas M (combined gas M+T) from the ion source 50 is maintained almost uniform by the flow resistance of the first aperture 111, the second aperture 112, and the like.

Figure 7:
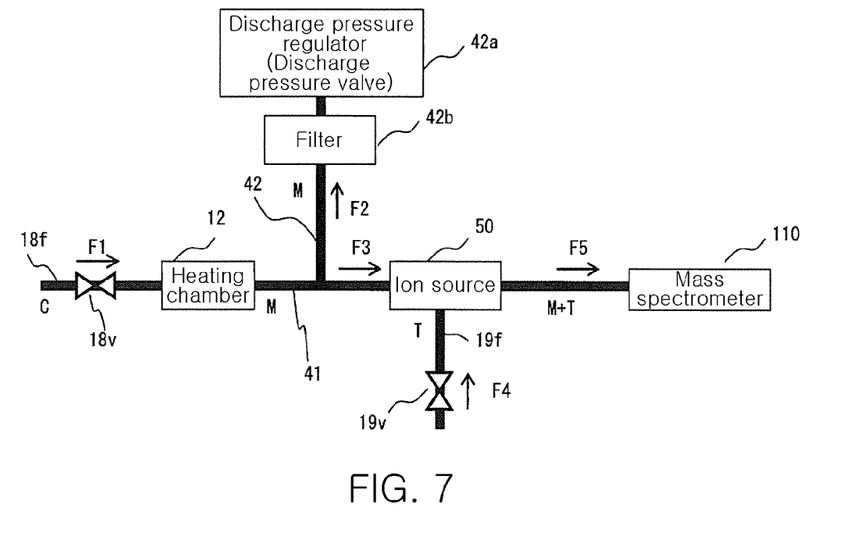
FIG. 7 schematically shows a process of adjusting the flow rate of a mixed gas flowing in a detection member.

FIG. 7 schematically shows the process of adjusting the flow rate of the mixed gas M (combined gas M+T) introduced to the ion source 50 from the mixed gas channel 41.

The split ratio SP of the flow rate F3 of the mixed gas M+T introduced to the ion source 50 relative to the flow rate F1 of the carrier gas C is represented as F3/F1.

Here, when the flow rate F1 is maintained constant C1 using the control valve 18v, SP is as follows.

$$SP=F3/F1=F3/C1 \qquad \text{Equation 1:}$$

Also, F3+F4=F5=C2 (constant), and thus Equation 1 is as follows.

$$SP=F3/C1=(C2-F4)/C1 \qquad \text{Equation 2:}$$

As is represented in Equation 2, in the present embodiment, the flow rate F4 of the inert gas T is adjusted using the control valve 19v, and thus the split ratio SP may be controlled, whereby it is easy to produce, no limitations are imposed on setting the flow resistance due to the dimensions of the apparatus, and the split ratio SP may be easily adjusted, compared to when the split ratio SP is controlled by adjusting the diameter (flow resistance) of the mixed gas channel 41 and the branch channel 42. Furthermore, when the split ratio SP is physically controlled by adjusting the diameter (flow resistance) of the mixed gas channel 41 and the branch channel 42, it is difficult to change the split ratio SP in subsequent procedures, but in the present embodiment, the split ratio SP may be freely controlled in subsequent procedures by adjusting the opening ratio of the control valve 19v.

The inert gas T is allowed to flow in the mixed gas channel 41 downstream of the branch channel 42, whereby flow resistance that suppresses the flow rate F3 of the mixed gas M introduced to the ion source 50 may result, making it possible to adjust the flow rate F2 of the mixed gas M discharged from the branch channel 42. Based on Equation 2, as the flow rate F4 increases, the split ratio SP decreases, that is, the mixed gas M is discharged in a larger amount from the branch channel 42.

When the gas component is evolved in a large amount and thus the gas concentration becomes too high, the flow rate of the mixed gas discharged outside of the branch channel is increased, whereby the flow rate of the mixed gas introduced from the gas channel to the detection member is reduced. Accordingly, the problem of inaccurate measurement due to over-scale of the detection signal that exceeds the detection range of the detection member may be solved.

Here, the inert gas T is allowed to flow only in a relatively small amount as the flow resistance that suppresses the flow rate F3, and there is no need to increase the flow rate of the carrier gas or the flow rate of the inert gas, and thus the precision of detection of the gas component may be improved without increasing the supply capacity of the carrier gas or inert gas and without enlarging the apparatus. Furthermore, since there is no need to dilute the gas concentration with a large amount of carrier gas or inert gas, enlargement of the apparatus due to an increase in the amount of gas introduced into the mass spectrometer 110 may be avoided.

Also, in the pipe in which the discharge side of the branch channel 42 is exposed, the flow rate F2 of the mixed gas M discharged from the branch channel 42 may become different from a theoretical value determined based on the split ratio SP due to variation in atmospheric pressure with climate. Thus, the discharge pressure of the mixed gas M discharged from the branch channel 42 is adjusted using the back pressure valve 42a or the like (the mixed gas M is discharged from the branch channel 42 when exceeding a predetermined pressure), whereby the influence of variation in atmospheric pressure may be suppressed, thus further improving the precision of detection of the gas component.

As described above, the mass spectrometer 110 becomes negative pressure (vacuum suction), and the flow rate F5 is maintained almost constant. However, a flow meter cannot be provided between the ion source 50 and the mass spectrometer 110, making it difficult to directly measure the flow rate F5.

Meanwhile, since the flow rate F4 is already known, the flow rate F5 may be determined in real time by (1) directly measuring the flow rate F3 or (2) measuring the flow rate F2 and calculating F3 based on the relationship of F1=F2+F3.

However, in the case of (1), a high-temperature gas containing a large amount of extract from the sample may come into contact with the flow meter provided directly before the ion source 50, which may thus cause malfunction of the flow meter. Therefore, the flow meter is provided to the branch channel 42 by employing (2), and the filter 42b is additionally disposed upstream of the back pressure valve 42a to thereby remove impurities from the mixed gas, and thus operation failure of the flow meter may be prevented.

When a mass spectrometer is used as an analysis apparatus, the gas component is ionized by the ion source 50 at the front thereof, but when the gas component is evolved in a large amount, the above-described ion suppression occurs due to ionization of the accessory component, and thus the detection signal is somewhat degraded.

In the case where ion suppression occurs, the flow rate control unit 216, which receives the peak intensity of the detection signal of the mass spectrometer 110 from the detection signal determination unit 214, determines that the peak intensity of the detection signal is less than the threshold value, thereby transmitting a control signal for increasing the opening ratio of the control valve 19v. Accordingly, since the flow rate of the mixed gas M introduced into the ion source 50 is reduced, the ionization of the accessory component is suppressed, and the degradation of the detection signal is prevented, thereby improving the precision of detection of the gas component.

Moreover, it cannot be known whether or not ion suppression occurs based only on the peak intensity of the detection signal, and there is a case where the amount of the gas component, which is the measurement target, is small. Therefore, it is necessary to judge the presence or absence of ion suppression based on other phenomena, such as the presence of a high concentration of impurities other than the measurement target. This judgment may be made by the operator or by the flow rate control unit 216, based on a table in which the presence or absence of ion suppression for each sample or gas component is stored, as will be described later.

The flow rate control unit 216 generates a control signal that increases the flow rate of the mixed gas M discharged from the branch channel 42 to the outside by increasing the opening ratio of the control valve 19v when the peak intensity of the detection signal exceeds the threshold value (over-scaled) or when the peak intensity is less than the threshold value (when it is determined that ion suppression is occurring), thus generating.

In this case, for example, the presence or absence of ion suppression for every gas component is stored in a table, and the flow rate control unit 216 determines the presence or absence of ion suppression with reference to this table. When ion suppression is determined to occur, a control signal for increasing the opening ratio of the control valve 19v may be transmitted to the control valve 19v. Also, whenever the measurement is conducted, the user inputs whether the measurement causes ion suppression or not using an input unit (select button, etc.) of the computer 210. The flow rate control unit 216 compares the peak intensity of the detection signal with the threshold value based on the input signal and transmits a control signal for increasing the opening ratio to the control valve 19v.

Also, a case in which the measurement target is phthalate and the accessory component is an additive such as phthalic acid, etc., can be exemplified as the case in which ion suppression occurs.

The present invention is not limited to the aforementioned embodiments, and it goes without saying that various modifications and equivalents are included in the spirit and scope of the present invention.

Examples of the measurement target include, but are not limited to, brominated flame retardants (polybrominated biphenyl (PBB) and polybrominated diphenyl ether (PBDE)), which are restricted under the Restriction of Hazardous Substances (RoHS) adopted by the European Union, in addition to phthalates.

The configurations, shapes, arrangements, and the like of the junction 45, the mixed gas channel 41, the branch channel 42, and the splitter 40 are not limited to the above examples. The detection member is not limited to the mass spectrometer.

The gas component evolving unit is not limited to the heating furnace 10, and may be a solvent-extraction-type GC/MS or LC/MS, in which a solvent containing a gas component is introduced and thus the gas component is evolved while volatilizing the solvent.

Although the flow rate F1 of the carrier gas C is adjusted using the first flow rate regulator 18v so as to be constant, when the flow rate F1 is changed, the flow rate control unit 216 may control the first flow rate regulator 18v.

The split ratio SP described above is set based almost entirely on the gas component to be measured, and the split ratio SP is set depending on the requirements of the customer at the time of shipment of the apparatus for analyzing an evolved gas. However, there is a desire to analyze other gas components after purchasing the apparatus for analyzing an evolved gas. Thus, for example, by replacing or adding the data file in which the split ratio SP is recorded, it is possible to analyze various gas components using a single apparatus.

The flow rate control unit 216 reads the data file and adjusts the flow rate F4.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An apparatus for analyzing an evolved gas, comprising:
   a gas component evolving unit configured to evolve a gas component contained in a sample,
   a detection member configured to detect the gas component evolved from the gas component evolving unit, and
   a mixed gas channel configured to connect the gas component evolving unit and the detection member to each other and to allow a mixed gas comprising the gas component and a carrier gas for guiding the gas component to the detection member to flow therethrough,
   and further comprising:
   a branch channel branched from the mixed gas channel and open to an outside,
   an inert gas channel joined to the detection member downstream of the branch channel such that an inert gas is allowed to flow therethrough to the detection member,
   a first flow rate regulator configured to adjust a flow rate F1 of the carrier gas,
   a second flow rate regulator configured to adjust a flow rate F4 the inert gas flowing through the inert gas channel, and
   a flow rate control unit configured to control a split ratio using the second flow rate regulator, thereby controlling a flow rate of the mixed gas guided to the detection member to a predetermined value,
   wherein the detection member is a mass spectrometer, and an ion source is provided between the mixed gas channel and the mass spectrometer so as to ionize the gas component of the mixed gas, the inert gas is allowed to flow to the ion source of the spectrometer, and a junction at which the inert gas channel is joined to the mixed gas channel is configured to be open to the outside downstream of the branch channel, the junction comprising a hole in a housing unit of the apparatus that couples a longitudinal end of the mixed gas channel with an end portion of the inert gas channel.

2. The apparatus of claim 1, wherein a discharge pressure regulator for adjusting a discharge pressure of the mixed gas discharged from the branch channel is provided at a discharge side of the branch channel.

3. The apparatus of claim 1, wherein the flow rate control unit controls the first flow rate regulator so as to increase the flow rate F1 when a detection signal from the detection member is less than a predetermined range.

4. The apparatus of claim 2, wherein the detection member is a mass spectrometer, and an ion source is provided between the mixed gas channel and the mass spectrometer so as to ionize the gas component of the mixed gas, and the flow rate control unit controls the first flow rate regulator so as to increase the flow rate F1 when a detection signal from the detection member is less than a predetermined range.

5. The apparatus of claim 3, further comprising a flow rate measurement instrument for measuring the flow rate of the mixed gas flowing into the detection member or the flow rate of the mixed gas discharged from the branch channel.

6. The apparatus of claim 4, further comprising a flow rate measurement instrument for measuring the flow rate of the mixed gas flowing into the detection member or the flow rate of the mixed gas discharged from the branch channel.

\* \* \* \* \*